United States Patent [19]
Lopez-Claros

[11] Patent Number: 5,562,719
[45] Date of Patent: Oct. 8, 1996

[54] LIGHT THERAPY METHOD AND APPARATUS

[76] Inventor: Marcelo E. Lopez-Claros, 871 Washington St., Raleigh, N.C. 27605

[21] Appl. No.: 398,603

[22] Filed: Mar. 6, 1995

[51] Int. Cl.$^6$ .................................................... A61N 5/06
[52] U.S. Cl. ................................................ 607/88; 600/27
[58] Field of Search .................... 607/88–91; 600/26, 600/27

[56] References Cited

U.S. PATENT DOCUMENTS

| | | | |
|---|---|---|---|
| 5,046,494 | 9/1991 | Searfoss et al. | 607/88 |
| 5,047,006 | 9/1991 | Brandston et al. | 607/91 |
| 5,137,018 | 8/1992 | Chuprikov et al. | 607/88 |
| 5,447,527 | 9/1995 | Waldman | 607/88 |
| 5,503,637 | 4/1996 | Kyricos et al. | 607/88 |

*Primary Examiner*—Angela D. Sykes
*Assistant Examiner*—Robert L. Nasser, Jr.
*Attorney, Agent, or Firm*—Rhodes, Coats & Bennett, L.L.P.

[57] ABSTRACT

Disclosed is a method and apparatus for the treatment of a variety of biopsychiatric disorders, for example Seasonal Affective Disorder, by preferentially directing light therapy to the non-dominant hemisphere of the brain. Specifically, the visual fields associated with the non-dominant cerebral hemisphere are stimulated to a greater degree than the visual fields associated with the dominant cerebral hemisphere by taking advantage of the characteristics of the human optical system, including the visual fields, the retina and its neuronal connections, and the distribution of neuronal pathways and their crossing at the optic chiasm before eventual arrival at the brain. The preferred apparatus for carrying out the method of the invention includes a mask-like device positioned in front of the patient's eyes that provides therapeutic illumination preferentially to the visual fields associated with the patient's non-dominant cerebral hemisphere by dividing the visual field of each eye into temporal and nasal visual fields. The apparatus includes two sets of two chambers, a temporal and a nasal chamber in front of each eye, that are each open to the respective eye at one end and separated from one another by divide, which divide the visual fields. The dividers are adjustable so that the device can be adapted to accommodate varying interpupillary distances from patient to patient.

9 Claims, 2 Drawing Sheets

5,562,719

LIGHT THERAPY METHOD AND APPARATUS

FIELD OF THE INVENTION

The present invention generally pertains to a method and apparatus for providing light therapy to a patient and more particularly pertains to a method and apparatus for treating a variety of psychiatric disorders, for example Seasonal Affective Disorder, by providing preferential photostimulation to the non-dominant cerebral hemisphere.

BACKGROUND OF THE INVENTION

Findings in the medical field have documented the importance of light in the stability of a person's energy, mood, sleep, concentration, and in the regulation of the person's circadian rhythms. Light deprivation has been shown to cause what is generally known as winter depression or Seasonal Affective Disorder, which is manifested by symptoms including fatigue, irritability, anxiety, weight gain, social withdrawal, and a lack of alertness. This condition affects from five to twenty percent of the population, with prevalence rates being the greatest in high latitude regions of the world. In the northern hemisphere, people suffering from Seasonal Affective Disorder generally experience a decline in mood around October that usually resolves by April. Other commonly affected people include those living in frequently overcast areas and night-shift workers.

As with many biopsychiatric disorders, Seasonal Affective Disorder is theorized to be related to neurotransmitter levels in the brain. For example, serotonin and serotonin pathways have been implicated in depressive disorders. The production of melatonin, which is a metabolite of serotonin and is synthesized in the pinealcytes, is apparently influenced solely by the light-dark cycle. In most animals, melatonin production begins in the evening, during which time melatonin levels abruptly rise in concentration. The melatonin levels peak during the night and then decline to a low, daytime concentration before dawn.

The production of melatonin from the pineal gland is stimulated by sympathetic neuronal output from the suprachiasmatic nuclei. This appears to function as an internal pacemaker or body clock located in the hypothalamus. The body clock is regulated by the light-dark cycle as sensed by the visual system. Photic input transmitted by the retinohypothalamic tract synchronizes the suprachiamatic nuclei to the light-dark cycle.

Increasing evidence points towards the non-dominant hemisphere of the brain as the primary site where mood is regulated, with a lesser contribution from the dominant hemisphere. In fact, a host of psychiatric disorders such as depressive disorders, anxiety disorders, affective disorders, sleep disorders, impulse control disorders, eating disorders, addictive disorders, obsessive disorders, impulse control disorders and learning disorders may be due to an imbalance of functioning between the non-dominant and the dominant cerebral hemispheres.

Light therapy has been successfully used to treat patients afflicted with Seasonal Affective Disorder. Light therapy typically involves the exposure of such patients to approximately one hour of light either in the morning or evening depending on the manifestations of their affliction. Commercially available lamps or light boxes generally provide from 2,500 to 10,000 lux illumination in an attempt to simulate summer light levels. Most light boxes include panels of light bulbs covered with a sheet of plexiglass that diffuses the light and a parabolic reflector to focus the light in the direction of the patient. Examples of apparatuses for providing light therapy are disclosed in the following United States patents: U.S. Pat. No. 5,343,121 to Terman, et al.; U.S. Pat. No. 5,292,345 to Gerardo; U.S. Pat. No. 5,149,184 to Hughes, et al.; and U.S. Pat. No. 5,047,006 to Brandston, et al.

Dr. Marcelo Enrique Lopez-Claros, postulates that light therapy directed predominantly or exclusively to the non-dominant cerebral hemisphere will lead to photic stimulation and thereby metabolic stimulation primarily in the non-dominant cerebral hemisphere, ultimately resulting in the correction of the imbalances present in the aforementioned disorders. Currently available light therapy devices, including the aforementioned patented apparatuses, are incapable of selectively stimulating the nondominant hemisphere. Rather, currently available light therapy devices stimulate both cerebral hemispheres essentially equally.

SUMMARY AND OBJECTS OF THE INVENTION

The present invention is a light therapy method and apparatus for the treatment of psychiatric disorders, such as Seasonal Affective Disorder, by preferentially directing photostimulation to the non-dominant hemisphere of the brain. The present invention works by taking advantage of the characteristics of the human optical system, including the locations of the visual fields, the retina and its neuronal connections, and the distribution of neuronal pathways and their crossing at the optic chiasm before eventual arrival at the brain. Specifically, photostimulation in the temporal visual field of the left eye and in the nasal visual field of the right eye leads to therapeutic stimulation of the right cerebral hemisphere, usually the non-dominant hemisphere in right-handed individuals. Conversely, photostimulation in the temporal visual field of the right eye and in the nasal visual field in the left eye leads to therapeutic stimulation of the left cerebral hemisphere, usually the non-dominant hemisphere in left-handed individuals.

A preferred apparatus for carrying out the method of the invention comprises a device positioned in front of the patient's eyes that provides therapeutic illumination preferentially to the visual fields associated with the patient's non-dominant cerebral hemisphere. A preferred apparatus includes two sets of two chambers, a temporal and a nasal chamber in front of each eye, which are each open to the respective eye at one end and separated from one another by dividers. Selected chambers include therapeutic illumination sources. Such an apparatus therefore divides the visual field of each eye into temporal and nasal visual fields.

In view of the above it is therefore an object of the present invention to provide a method for treating psychiatric disorders such as Seasonal Affective Disorder by providing preferential photostimulation to a patient's non-dominant cerebral hemisphere.

Another object of the present invention is to provide a method for treating psychiatric disorders such as Seasonal Affective Disorder by dividing a patient's visual fields into temporal and nasal visual fields, then preferentially providing therapeutic illumination in the visual fields associated with the non-dominant cerebral hemisphere.

Another object of the present invention is to provide an apparatus that achieves the above-stated objectives.

Another object of the present invention is to provide such an apparatus that is adjustable to fit different patients with different interpupillary distances.

DETAILED DESCRIPTION OF THE INVENTION

Figure 1:
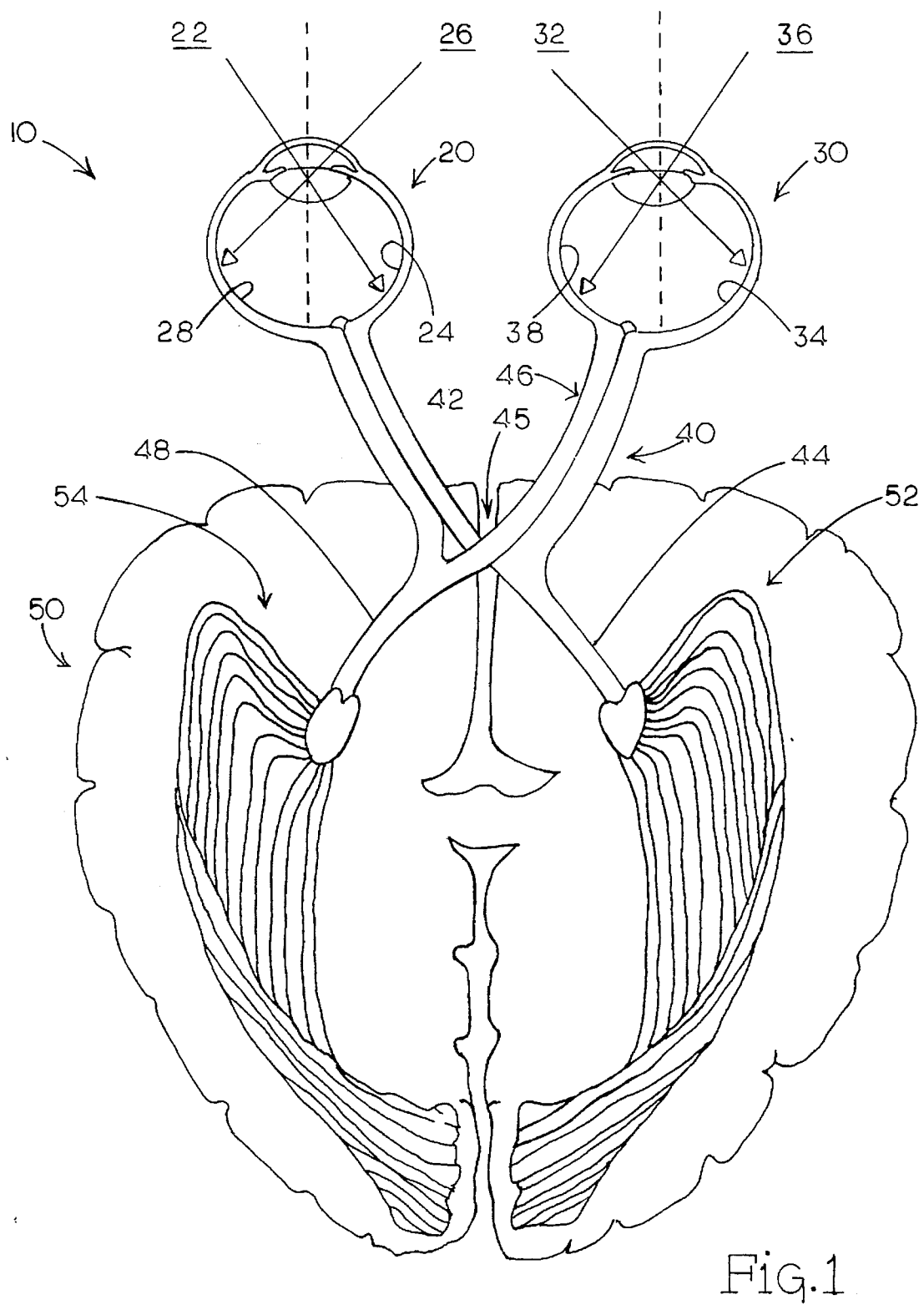
FIG. 1 is a representation of the neurological anatomy of the optical system and the relation of the visual fields thereto.

The present invention provides a method and apparatus for treating psychiatric disorders, such as Seasonal Affective Disorder, by preferentially stimulating a patient's nondominant cerebral hemisphere with light. To better understand the neurological basis for differentiation between cerebral hemispheres, it is helpful to review the neurology of the optic system, indicated generally by the numeral 10. By studying FIG. 1, which depicts the neurology of the optical system, the paths of visual sensation can be traced back through the eyes 20, 30, the nerves 40, and finally to the brain 50. To begin, light from the left temporal visual field 22 stimulates the nasal retina 24 of the left eye 20, which then outputs a signal through the left optic nerve 42 to the optic chiasm 45 from which the signal then passes through the right optic tract 44 to the right cerebral hemisphere 52. Moving to the right in FIG. 1, light from the left nasal visual field 26 stimulates the temporal retina 28 of the left eye 20, which then outputs a signal through the left optic nerve 42 to the optic chiasm 45 from which the signal then passes through the left optic tract 48 to the left cerebral hemisphere 54. Light from the right nasal visual field 32 stimulates the temporal retina 34 of the right eye 30, which then outputs a signal through the right optic nerve 46 to the optic chiasm 45 from which the signal then passes through the right optic tract 44 to the right cerebral hemisphere 52. Finally, light from the right temporal visual field 36 stimulates the nasal retina 38 of the right eye 30, which then outputs a signal through the right optic nerve 46 to the optic chiasm 45 from which the signal then passes through the left optic tract 48 to the left cerebral hemisphere 54. The end result of this neurological configuration is that visual stimulation from the left visual field of each eye will reach the right cerebral hemisphere 52, whereas visual stimulation from the right visual field of each eye will reach the left cerebral hemisphere 54.

The method of the present invention takes advantage of the neurology of the optic system 10 to provide photostimulation primarily or entirely to the non-dominant hemisphere of the brain. Because the right cerebral hemisphere 52 is the non-dominant hemisphere in most of the population, for convenience, this description will primarily focus on the embodiment of the invention that provides photostimulation preferentially to the right cerebral hemisphere 52. However, it should be understood that the method and apparatus of the invention can simply be reversed to provide photostimulation preferentially to the left cerebral hemisphere 54.

The method of the present invention for treating Seasonal Affective Disorder in a patient by using light therapy involves preferentially providing therapeutic illumination to the visual fields associated with the non-dominant cerebral hemisphere, such that the visual fields associated with the non-dominant cerebral hemisphere are illuminated to a greater degree than the visual fields associated with the dominant cerebral hemisphere. In the greatest percentage of cases, where the patient's right cerebral hemisphere 52 is the non-dominant hemisphere, the temporal visual field 22 of the patient's left eye 20 and the nasal visual field 32 of the patient's right eye 30 are provided with greater intensity illumination than the nasal visual field 26 of the patient's left eye 20 and the temporal visual field 36 of the patient's right eye 30. In the smaller percentage of cases, where the patient's left cerebral hemisphere 54 is the non-dominant hemisphere, the nasal visual field 26 of the patient's left eye 20 and the temporal visual field 36 of the patient's right eye 30 are provided with greater intensity illumination than the temporal visual field 22 of the patient's left eye 20 and the nasal visual field 32 of the patient's right eye 30.

It is postulated that preferential direction of photostimulation to the non-dominant cerebral hemisphere more effectively stimulates neurotransmitter activity in the brain than conventional, non-differentiating light therapy that equally stimulates both cerebral hemispheres. Therefore, light therapy performed according to the method of the invention may provide an improved treatment for Seasonal Affective Disorder. The present invention may also be employed to better treat other biopsychiatric disorders associated with a lack of adequate environmental illumination such as depressive disorders, anxiety disorders, affective disorders, sleep disorders, impulse control disorders, eating disorders, addictive disorders, obsessive disorders, impulse control disorders, and learning disorders.

It is contemplated that the method of the invention may be practiced using a variety of apparatuses or devices that act to provide a greater intensity of therapeutic illumination in the visual fields and to the portions of the retinas associated with the non-dominant cerebral hemisphere. For example, it is contemplated that a patient suffering from Seasonal Affective Disorder could wear a pair of glasses or contact lenses having one half of each lens darkened to exclude light from the portions of the retinas associated with the dominant cerebral hemisphere. Other possible devices for carrying out the method of the invention could include a small light attached to one side of the head on a cap or other support structure.

Figure 2:
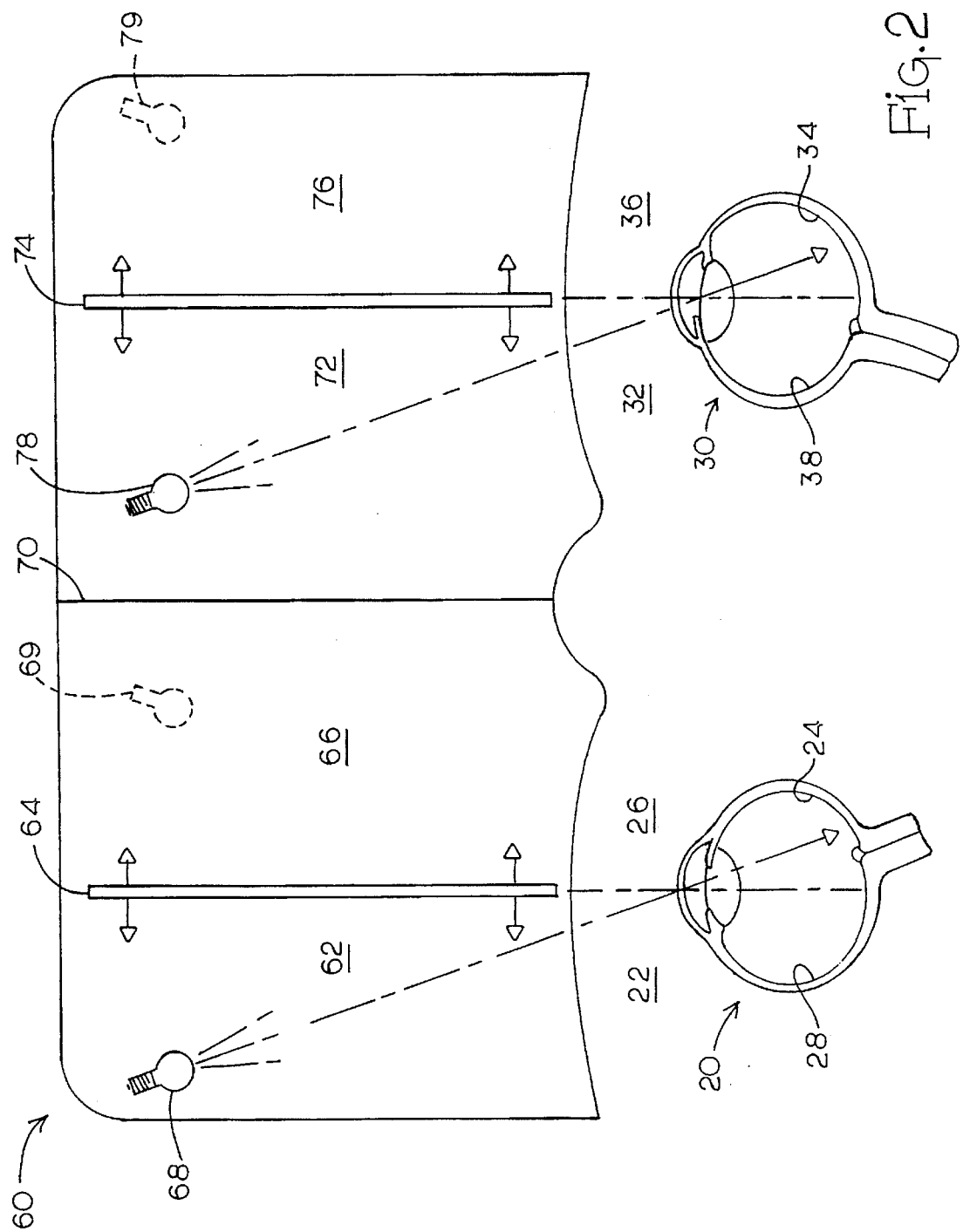
FIG. 2 is a schematic representation of an apparatus for carrying out the method of the invention.

FIG. 2 depicts a schematic representation of a preferred apparatus for providing differential light therapy to a patient having a non-dominant right cerebral hemisphere. As shown in FIG. 2, the apparatus of the invention comprises a mask, generally indicated by the numeral 60, positioned in front of the patient's eyes 20, 30 so as encompass the patient's visual fields. The mask 60 provides therapeutic illumination preferentially to the left temporal visual field 22 and the right nasal visual field 32 by dividing the visual field of each eye into temporal and nasal visual fields. The disclosed mask 60 includes four chambers, a left temporal chamber 62, a left nasal chamber 66, a right nasal chamber 72, and a right temporal chamber 76, which are each open to respective eyes 20, 30 at one end. Left divider 64 divides the visual fields 22, 26 of the left eye, whereas right divider 74 divides the visual fields 32, 36 of the right eye 30. A central divider 70 separates the visual fields of the left eye 20 from the visual fields of the right eye 30.

In the disclosed apparatus of the invention 60, therapeutic illumination sources 68, 78 are disposed in the left temporal chamber 62 and the right nasal chamber 72, respectively, to provide light therapy preferentially in those visual fields. Such illumination sources may be any conventional type of illuminating device suitable for providing light therapy, such as fluorescent lights with an intensity in the range of, for example, 2,500 to 10,000 lux. Preferably, the intensity and color of the illumination sources 68, 78 are independently adjustable so that light therapy can be varied between the eyes 20, 30. However, in most cases, the light would be the same for each eye. Optional secondary illumination sources 69 and 79 may be provided in, respectively, the left nasal chamber 66 and the right temporal chamber 76. To carry out the method of the invention, however, these additional illumination sources should emit light of a lesser intensity than illumination sources 68 and 78. As should be understood, with a patient with a non-dominant left cerebral hemisphere 54, the illumination sources would be disposed oppositely from what is shown in the depicted embodiment.

To divide the visual fields as completely as possible, so that therapeutic illumination in one visual field is substantially excluded from an adjacent visual field, the chamber walls 64, 74 should be positioned as close to the respective eyes 20, 30 as possible. To exclude extraneous environmental light, the mask 60 should be shaped to conform to the patient's face and should be open only on the side covering the patient's face. Additionally, the left wall 64 and right wall 74 should be adjustable so the device 60 can be adapted to fit varying interpupillary distances from patient to patient. To maintain optimal differentiation of light therapy to the non-dominant cerebral hemisphere, the mask 60 should be provided with a targeting and alignment structure that encourages the patient to maintain a fixed gaze straight ahead.

It is contemplated that the mask 60 could be connected to a light therapy controller, which would preferably include a microcomputer. The controller could be used to vary the intensity and/or color of the therapeutic illumination and could also be used to measure and record the patient's vital signs during a light therapy treatment session. Possible manners in which the therapeutic illumination could be varied include providing differential illumination intensities among the four visual fields or within a single visual field and/or varying the color among all the visual fields or within a single visual field. A feedback system could also be provided in the control module to automatically vary the therapeutic illumination in response to certain changes in the patient's vital signs. The vital signs could thus be correlated with parameters of the therapeutic illumination to attain an optimal therapeutic response for a particular patient.

The present invention may, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method for treating a psychiatric disorder using light therapy, comprising the steps of:
    a) dividing the visual fields of a patient's eyes into temporal and nasal visual fields; and
    b) illuminating the visual fields associated with the non-dominant hemisphere of the patient's brain with greater intensity illumination than is present in the visual fields associated with the dominant hemisphere of the brain.

2. The method of claim 1 wherein the psychiatric disorder includes Seasonal Affective Disorder.

3. The method of claim 1 wherein the therapeutic illumination has an intensity of at least 2500 lux.

4. The method of claim 1, further comprising the step of monitoring the patient's vital signs during the light therapy.

5. The method of claim 1, further comprising the step of varying the intensity of the therapeutic illumination.

6. The method of claim 1, further comprising the step of varying the color of the therapeutic illumination.

7. A method for treating psychiatric disorders in a patient by using light therapy, comprising the step of preferentially providing therapeutic illumination to the visual fields associated with the non-dominant cerebral hemisphere, such that the visual fields associated with the non-dominant cerebral hemisphere are stimulated to a greater degree than the visual fields associated with the dominant cerebral hemisphere.

8. The method of claim 7 wherein the patient's right cerebral hemisphere is the non-dominant hemisphere and wherein the step of providing therapeutic illumination comprises illuminating the temporal visual field of the patient's left eye and the nasal visual field of the patient's right eye with greater intensity illumination than the nasal visual field of the patient's left eye and the temporal visual field of the patient's right eye.

9. The method of claim 7 wherein the patient's left cerebral hemisphere is the non-dominant hemisphere and wherein the step of providing therapeutic illumination comprises illuminating the nasal visual field of the patient's left eye and the temporal visual field of the patient's right eye with greater intensity illumination than the temporal visual field of the patient's left eye and the nasal visual field of the patient's right eye.

\* \* \* \* \*